United States Patent
DeVet et al.

(10) Patent No.: US 8,376,228 B2
(45) Date of Patent: Feb. 19, 2013

(54) PRODUCT IDENTIFICATION AND TRACKING

(75) Inventors: Roberto DeVet, Minneapolis, MN (US); Molly Condon, Minnetonka, MN (US); Erik Bilicki, Saint Michael, MN (US)

(73) Assignee: Target Brands, Inc., Minneapolis, MN (US)

( * ) Notice: Subject to any disclaimer, the term of this patent is extended or adjusted under 35 U.S.C. 154(b) by 459 days.

(21) Appl. No.: 12/365,850

(22) Filed: Feb. 4, 2009

(65) Prior Publication Data

US 2009/0194587 A1    Aug. 6, 2009

Related U.S. Application Data

(60) Provisional application No. 61/026,009, filed on Feb. 4, 2008.

(51) Int. Cl.
*G06F 19/00* (2011.01)
(52) U.S. Cl. ........................ 235/385; 235/383
(58) Field of Classification Search ........... None
See application file for complete search history.

(56) References Cited

U.S. PATENT DOCUMENTS

| | | | |
|---|---|---|---|
| 5,151,684 A | | 9/1992 | Johnsen |
| 7,180,627 B2 | | 2/2007 | Moylan et al. |
| 7,837,107 B1 * | | 11/2010 | Leu et al. ............ 235/385 |
| 2002/0145037 A1 | | 10/2002 | Goodwin, III |
| 2004/0088231 A1 * | | 5/2004 | Davis, Jr. ............ 705/28 |
| 2006/0106718 A1 * | | 5/2006 | Spellman et al. ......... 705/50 |
| 2006/0213989 A1 | | 9/2006 | Ahmadi et al. |
| 2006/0266824 A1 | | 11/2006 | Hassenbuerger |
| 2007/0187266 A1 * | | 8/2007 | Porter et al. ............ 206/232 |
| 2007/0285242 A1 * | | 12/2007 | Higham ............ 340/572.1 |
| 2009/0002173 A1 * | | 1/2009 | Bergsten et al. ......... 340/572.1 |

OTHER PUBLICATIONS

Herbert, Ayisat. "BA Delivers First commercially Available Single Device E-Pedigree Solution." Upper Marlboro, MD; Jan. 4, 2008.
Dynasys RFID. "SIRIT Reader Modules." Retried on Nov. 23, 2007. Retrieved from the Internet: <URL: http://www.rfidusa.com/superstore/index.php?cPath=96>.
Unitech America, Inc. "RFID Solutions Online. Unitech RH767 RFID Portable Reader." Retrieved on Nov. 23, 2007. Retrieved from the Internet: <URL: http://www.rfidsolutionsonline.com/content/productshowcase.product.asp?docid=cf3569ea-9527-4adc-a>.

* cited by examiner

*Primary Examiner* — Thien M. Le
*Assistant Examiner* — Sonji Johnson
(74) *Attorney, Agent, or Firm* — Nixon & Vanderhye P.C.

(57) ABSTRACT

A system may be configured to identify pedigree information associated with a drug. The system may include a structure with an RFID reader and a bar code reader. The system may also include a master control unit configured to receive product identification data from the RFID reader and the bar code reader. The system may also include a database system configured to store pedigree information associated with medicament containers. The system may also include a display unit disposed proximate to the support structure, and the display unit may be configured to receive and display the pedigree information to a user. In response to the movement of a medicament container proximate the RFID reader or the bar code reader, the master controller may submit a query to the database system, receive the pedigree information, and cause the display unit to display a portion of the pedigree information to the user.

13 Claims, 7 Drawing Sheets

PRODUCT IDENTIFICATION AND TRACKING

CROSS-REFERENCE TO RELATED APPLICATION

This Application claims priority under 35 U.S.C. §119(e) to U.S. Provisional Application Ser. No. 61/026,009 titled "System and Method for Product Identification" filed on Feb. 4, 2008, the disclosure of which is incorporated herein by reference.

BACKGROUND

According to the FDA, counterfeit pharmaceutical drugs pose a significant threat to the public safety and to the integrity of the overall drug supply chain. Drug counterfeiting has increased in recent years, which is potentially related to the increased number of access points that exist in the supply chain for many of these drugs. Prescription pharmaceutical drugs are typically transferred between a number of different parties before they are eventually dispensed to a consumer. For example, a drug may be produced by a manufacturer, then handed off to a distributor, and then delivered to a pharmacy or other retailer before finally being dispensed to a consumer. With each of these transfers, and with every additional handler of the drugs, there is an inherent risk of potential foul play.

In an attempt to prevent or at least minimize drug counterfeiting and other improper drug transfers, many federal and state government agencies now require, or may soon require, that records of these drug transfers be tracked and maintained—essentially creating a chain of custody for the drug from the time it is produced until it reaches the consumer. This chain of custody information is often referred to as the pedigree of a drug, and it was traditionally maintained via inefficient paper documentation. Paper-based drug pedigrees allowed agencies to more efficiently track and prosecute counterfeiting activities, but did little to prevent such activities due to intrinsic delays associated with a paper-based system. More recently, the pedigree information is increasingly being stored in electronic form. These electronic records are often referred to as the electronic pedigree, or e-pedigree, of a drug.

SUMMARY

A system may be configured to identify pedigree information associated with a drug. The system may include a support structure including an RFID reader and a bar code reader. The system may also include a master control unit that is operably coupled to the RFID reader and the bar code reader. The master control unit may be configured to receive product identification data from the RFID reader and the bar code reader. The system may also include a database system communicatively coupled to the master control unit. The database system may be configured to store pedigree information associated with a plurality of medicament containers. For each of the medicament containers, the pedigree information may include at least two items selected from the following: i) a location and date of manufacture, ii) a batch number, iii) a previous storage location, iv) a quantity of drug in the container, and v) an expiration date. The system may also include a display unit operably coupled to the master control unit and disposed proximate to the support structure, and the display unit may be configured to receive and display the pedigree information to a user. In response to the movement of a medicament container proximate the RFID reader or the bar code reader, the master controller may submit a query to the database system, receive the pedigree information, and cause the display unit to display at least a portion of the pedigree information to the user. In various implementations, the system may also include an alarm adapted to notify the user if the pedigree information is incomplete.

One method of tracking drug containment units can include receiving, at a drug handling facility, a drug containment unit. The method can further include identifying the drug containment unit using a scanning system with an RFID reader, a barcode reader, a computing device configured to electronically communicate with a database system, and a display. Identifying the drug containment unit may include moving the drug containment unit proximate the RFID reader or the bar code reader. The method can also include querying the database system with the computing device to retrieve pedigree information associated with the drug containment unit. The pedigree information may include at least two data items selected from the group consisting of i) a location and date of manufacture, ii) a batch number, iii) a previous storage location, iv) a quantity of drug in the container, and v) an expiration date. The method may further include displaying at least a portion of the pedigree information on the display.

In various implementations, the method may also include updating the pedigree information to reflect that the drug containment unit has been received, printing the pedigree information on the drug containment unit, or entering into the scanning system handling information associated with a shipping container in which the drug containment unit was packaged.

Another method of tracking drug containment units can include receiving, at a drug handling facility, a drug containment unit. The method can further include identifying the drug containment unit using a scanning system having an RFID reader and a barcode reader. The method can also include querying a pedigree database to retrieve pedigree information associated with the drug containment unit. The pedigree information may include at least two data items selected from the group consisting of i) a location and date of manufacture, ii) a batch number, iii) a previous storage location, iv) a quantity of drug in the drug containment unit, and v) an expiration date. The method may further include displaying at least a portion of the pedigree information on a display.

In various implementations, the method may also include updating the pedigree information to reflect that the drug containment unit has been received, printing the pedigree information on the drug containment unit, or updating the pedigree information to reflect handling information associated with a shipping container in which the drug containment unit was packaged.

The details of one or more implementations are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION OF ILLUSTRATIVE IMPLEMENTATIONS

Figure 1:
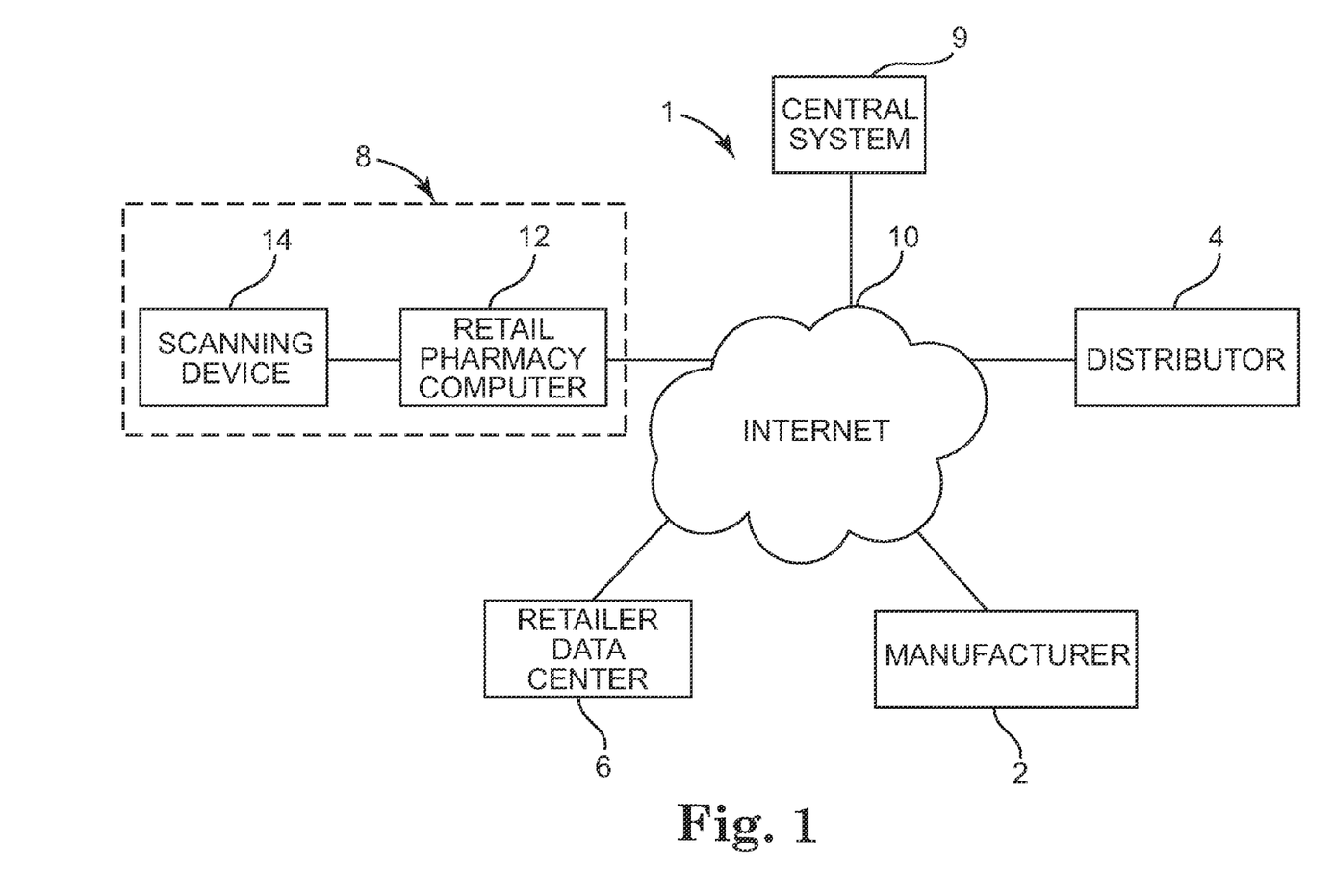
FIG. 1 is a conceptual diagram of a system for tracking items.

FIG. 1 shows a conceptual diagram of a system 1 for tracking items, such as a drug and its pedigree information. The tracking system 1 may include multiple parties or elements that, either separately or together, maintain data regarding the who, what, where, when, how, and/or why information related to an item throughout the entire lifecycle of the item. In certain implementations, such a tracking system 1 may be used to maintain the pedigree of a drug or to provide other similar tracking or handling information. Although this description focuses primarily on the use of such a system 1 for tracking and updating e-pedigree information for pharmaceutical drugs, it should be understood that the system 1 may also be used in other contexts where chain of custody or distribution information should be carefully tracked and maintained. As one example of an alternative context, the system 1 may be used to ensure proper handling and transfers of baby formula starting from the source of the formula, through any number of intermediaries, and until the product reaches the end consumer.

As shown in FIG. 1, a tracking system 1 may include separate data processing systems at a drug manufacturer 2, at a drug distributor 4, at a retailer data center 6, and at a retail pharmacy location 8. The tracking system 1 may also include more or fewer parties or elements than are shown in FIG. 1. For example, the tracking system 1 may include more than one drug manufacturer 2, more than one drug distributor 4, more than one retailer data center 6, and/or more than one retail pharmacy location 8. Alternatively, one or more of these elements, such as the drug distributor 4, may be omitted, for example, where a drug manufacturer 2 works directly with a retail pharmacy 8. The tracking system 1 may also include other relevant parties or elements, such as one or more separate shipping companies that transport the drug between the various parties. In some implementations, the parties or elements 2, 4, 6, 8 may be connected to one another via the Internet 10, or via some other electronic connection, to form a more integrated tracking system 1.

Information about the pedigree of a drug may be shared between the data processing systems of the various parties 2, 4, 6, 8 in order to maintain a complete drug pedigree. The sharing of this pedigree information may be done in a number of different ways. In one example, each party that takes possession of the drug may update the drug pedigree information so that the pedigree correctly reflects the chain of custody. When physically transferring the drug to a subsequent party in the chain of custody, the pedigree information may also be transferred to the subsequent party, and the subsequent party may update the pedigree information to reflect this change in possession. Depending on various requirements or the relevance of past data, the pedigree information may be stored by any of the previous parties for some length of time, or perhaps until the entity is advised that the data is no longer needed. Under this example, which closely mimics a paper-based pedigree system, the party that has physical possession of the drug also has the most updated drug pedigree information.

Another example of sharing the pedigree information may involve a central system 9 that maintains the entire history of the drug as well as the most up to date information available. Under this particular example, all of the pedigree information that is entered by any of the entities that handle a drug may automatically be uploaded via the Internet 10 to the central system 9 rather than, or in addition to, being stored at any of the respective data processing systems. In certain implementations, an integrated tracking system 1 may include a combination of features from either of these examples.

Pharmaceutical drugs may pass through many different entities or other intermediaries en route to the end user. For example, the drug manufacturer 2 may produce the drug and package it into one or more drug containment units. The drug containment units may include bottles, boxes, or other containers that hold a specific amount of the drug, and one or more of these drug containment units may be shipped together in a larger shipment of drugs. In some implementations, one or more drug containment units may be shipped together in a bulk shipment container, such as a tote. As further discussed below, the drug containment units may be transferred to and/or from a number of different parties before arriving at a retail pharmacy location 8. Then, at the retail pharmacy location 8, prescriptions may be dispensed to consumers from the one or more drug containment units.

Each drug containment unit may have one or more individual identifiers that can be used to track the drug containment unit as it is shipped from the manufacturer 2, through various intermediaries, and eventually to the retail pharmacy location 8. The individual identifier may, for example, include an identifier that is associated with a barcode (e.g., a 1-dimensional barcode, a 2-dimensional barcode, a data matrix barcode, etc.). The identifier may also include an Electronic Product Code (EPC) that may be associated with a UHF or an HF RFID tag. As discussed in greater detail below, a drug containment unit may have multiple modes of identification (e.g., both a barcode and an RFID tag), and the identifiers associated with the different modes of identification may be the same or different.

As part of the pedigree of a drug, a manufacturer 2 may store information related to the manufacturing of the drug, and may associate that information with a drug containment unit. This pedigree may include, for example, any combination of the following data: the National Drug Code (NDC), the name of the drug, a description of the drug, the location and date of manufacture, the batch number of the drug, the location(s) of storage while the manufacturer had possession of the drug, the conditions of manufacture and/or storage of the drug, the amount of the drug contained in a drug containment unit, the unit of measure for the drug (e.g., number of pills, fluid ounces, or mass ounces), and/or an expiration date for the drug containment unit. When the drug is physically transferred to a drug distributor 4, the drug pedigree information may be transmitted from the data processing system at the drug manufacturer 2 to the data processing system at the drug distributor 4.

The manufacturer 2 and/or the drug distributor 4 may also add information to the drug pedigree regarding the physical transfer of the drug from the manufacturer to the drug distributor, thus creating an updated drug pedigree. For example, the drug distributor 4 could add any of the following information to the drug pedigree: the date of receipt of the drug, the individuals who had physical custody of the drug during transfer, and/or the one or more locations at which the drug containment unit was stored while the drug distributor 4 had possession of the drug.

Likewise, when the drug is transferred from the drug distributor 4 to a retail pharmacy location 8, the drug pedigree information may be transmitted from the data processing system at the drug distributor 4 to the data processing system at the retail pharmacy location 8. Information regarding this transfer may be added to the drug pedigree, once again creating an updated drug pedigree. As further discussed below, the drug pedigree information may then be used by or further amended at the retail pharmacy location 8.

In certain implementations, the retail pharmacy location 8 may also have an associated retailer data center 6, where the pedigree information of the drugs in the pharmacy may be stored. The drug pedigree information at the retail pharmacy location 8 or the other previous handlers 2, 4 may also be backed up by storing the drug pedigree information at another location, for example at an e-pedigree central system 9.

While the tracking system 1 is generally described as continuously updating the drug pedigree as the drug physically moves through the chain of custody, the tracking system 1 could also operate and provide updates in other ways. For example, the data processing systems at one or more of the parties 2, 4, 6, 8 could maintain only the portion of the drug pedigree corresponding to the time during which that particular party had actual physical custody of the drug. If the drug pedigree information is desired at any time, each of the data processing centers at any of the various locations 2, 4, 6, 8 may be queried, and the drug pedigree may be assembled using the information returned from the separate parties.

The tracking system 1 may also have a central system 9 that comprises a central data processing system for tracking and storing e-pedigree information. When information relating to a drug pedigree is generated by any of the parties 2, 4, 6, 8, the information may also be sent to this central system 9. In various implementations, the pedigree information may be sent in batches to the central system 9, or the data may be fed in near real-time soon after any updates to a drug's pedigree have been made. One benefit of updating the central system 9 as described in the latter example is that it ensures that the central system always has the most updated pedigree information available at any given time.

Upon receiving individual portions of pedigree information, such as via pedigree updates as described above, the central system 9 may compile the complete drug pedigree information received from all of the parties involved in the chain of custody. If the drug pedigree is required, for example by a drug auditor, the central system 9 may be queried for the most recent version of the pedigree information. Such a central system 9 may allow for more efficient querying of pedigree information by circumventing the need to query each of the different previous handlers to obtain a complete drug pedigree. As the tracking system 1 becomes more complex with greater numbers of manufacturers, distributors, retailers, or other handlers, such a central system 9 may provide a significant benefit.

Information regarding the pedigree of a drug may also be received by the data processing system at the retail pharmacy location 8 directly from one or more of the other drug handlers in the tracking system 1, for example directly from the manufacturer 2 and/or the distributor 4. This information may be received after a query has been sent out to the other elements of the tracking system 1 (i.e., the data may be "pulled" in by the data processing system at the retail pharmacy location 8) or the information may be automatically sent from the other intermediaries (i.e., the data may be "pushed" out to the retail pharmacy location 8 from a party that previously had physical possession of the drug).

As shown in FIG. 1, the data processing system at the retail pharmacy location 8 may include a retail pharmacy computer 12 and a scanning device 14. The other entities may also have their own scanning devices. The scanning device 14 may be used to scan drugs that have been received at the retail pharmacy location 8. Once the drug has been received and scanned using a process that will be further discussed below, the drug pedigree information may be updated to reflect the receipt of the drug at the retail pharmacy location 8. In implementations where the drug pedigree is backed up at a retailer data center 6, this updated pedigree information may also be sent to the retailer data center 6. In some cases, after a certain time (e.g., 30 days), the pedigree information may be deleted from the data processing system at the retail pharmacy location 8 in order to maintain adequate electronic storage capacity for the pedigree information of newly arriving drugs.

Figure 2:
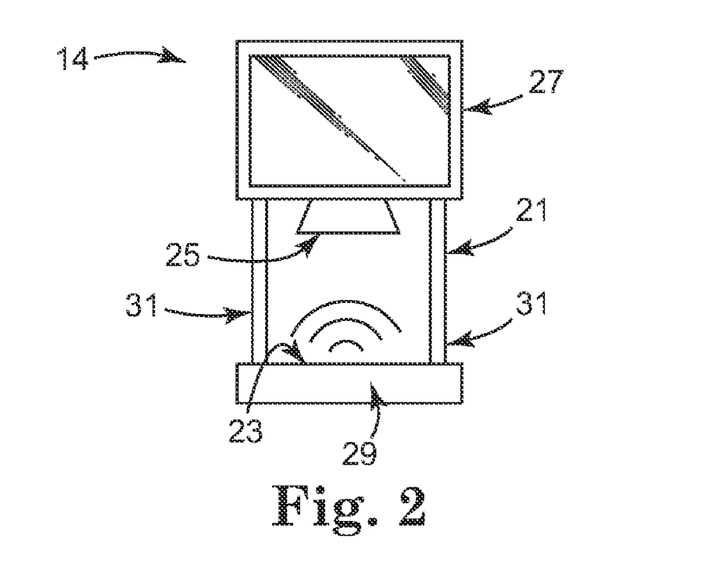
FIG. 2 is a front view of an example scanning device.

FIG. 2 shows a front view of an example scanning device 14, according to certain implementations. The scanning device 14 is shown with a support structure 21, an RFID reader 23, a barcode reader 25, and a display 27. The support structure may include a base 29 and, extending vertically from the base 29, one or more vertical supports 31. The RFID reader may be disposed in an RFID reader pad in the base 29. The barcode reader 25 may be disposed above the base 29, for example, on a horizontal support 33 that is attached to the vertical supports 31. In addition, the screen of the display 27 may be visible to a user who is positioned towards the front of the scanning device 14.

Figure 3:
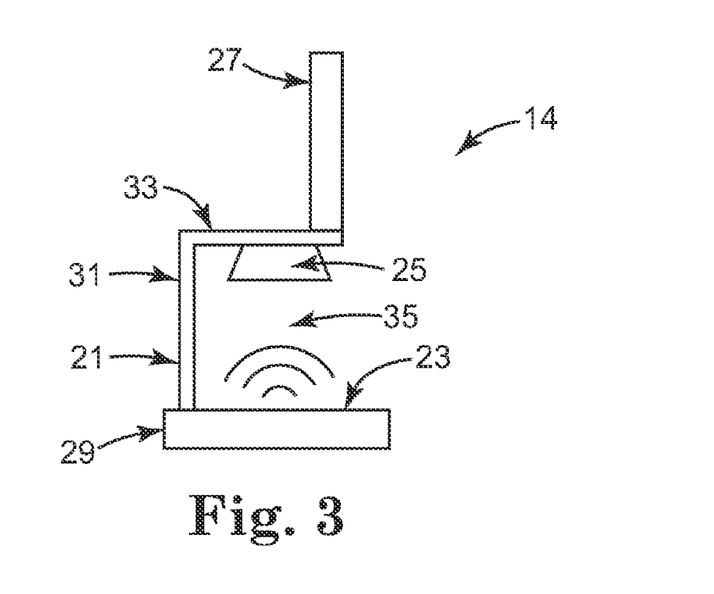
FIG. 3 is a side view of the example scanning device of FIG. 2.

As further shown in the side view of FIG. 3, the support structure 21 of the scanning device 14 may have one or more horizontal supports 33 that may support the display 27 and the barcode reader 25. The vertical supports 31, the horizontal supports 33, and the base 29 together form an open area 35 through which a single drug, a drug containment unit, or a tote may be passed. As a drug containment unit is passed through the open area 35, the RFID reader may receive information from an RFID tag on the drug containment unit and/or the barcode reader may receive information from a barcode on the drug containment unit.

The configuration of the scanning device 14 shown in FIGS. 2 and 3 may allow for the user to operate the device essentially hands-free, thus allowing the user to handle the drug containment units more carefully and with both hands if necessary. In other words, the user does not have to hold the RFID reader or barcode scanner in one hand, or push a button on the RFID reader or the barcode reader in order to obtain a proper scan. Instead, the scanning device 14 may continuously monitor for items passed through its scanning field, and may properly identify any item that passes within reach of the field.

The information from the RFID tag or barcode may contain a unique identifier for the drug containment unit. As discussed in more detail below, the scanning device 14 may use this information to retrieve and display drug pedigree information to a user. Whether the drug containment unit has a barcode or an RFID tag, the scanning device 14 may be configured to scan the drug containment unit with both the barcode reader and the RFID reader at the same time, with a single sweep of the drug containment unit through the open area 35 of the scanning device 14.

In some implementations, the RFID reader may include a high frequency RFID reader, for example operating at 13.56 MHz. In other implementations, the RFID reader may include an ultra high frequency (UHF) RFID reader, for example operating above 850 MHz, or in the range of 902-928 MHz. In other implementations, the RFID reader may include both an HF and a UHF reader, and in some cases may simultaneously operate as both an HF and a UHF RFID reader at the frequency ranges mentioned above. The RFID reader's operating frequency, along with other parameters of the reader, may determine the detection range of the reader. For example, the RFID reader 23 may have a detection range of about 12 inches or less, or about 6 inches or less, or about an inch or less. In some implementations, the RFID reader may have a detection range that requires the package of drugs to essentially be contacted with the RFID device to detect the RFID identifier.

Although the scanning device 14 has been discussed and presented as shown in FIGS. 2 and 3, the scanning device 14 may have other useful configurations. For example, the RFID reader 23 and the barcode reader 25 may be located in the same reader pad on one surface of the scanning device 14, for example on the base 29 of the scanning device 14. As another example, the display 27 may have a separate base, allowing the display to be placed near the readers, for example on a countertop next to the readers. One advantage of having a display that is separate from the support structure 21 is that any standard display device may be used with the system without any modification to the support structure 21 of the scanning device 14.

In addition to the other parts mentioned above, the scanning device 14 may also include a computer or other computing device. The computer may be connected to the RFID reader, the barcode reader, and the display, and may control the operation of the scanning device 14. The computing device may also be used to store and update the pedigree information, as will be described in greater detail below. As shown in FIG. 1, the data processing system at the retail pharmacy location 8 may have a retail pharmacy computer 12. The retail pharmacy computer 12 may be the computer that operates the scanning device 14, or the scanning device 14 may have a separate computer that communicates with the retail pharmacy computer 12. In implementations where the retail pharmacy computer 12 operates the scanning device 14, the retail pharmacy computer 12 may be considered to be a part of the scanning device 14.

Drug pedigree information may be received from other elements of the tracking system 1 directly from the scanning device 14. Or, if the retail pharmacy computer 12 is a separate computer from the scanning device 14, the drug pedigree information may be received by the retail pharmacy computer 12. Use of the scanning device 14 to scan the drug and process the drug pedigree information is discussed in greater detail below.

The scanning device 14 may also include other appropriate input devices, such as a keyboard and a mouse, for example. In certain implementations, the display 27 may be a touch screen and therefore the display 27 may also act as an input device. Each of these input devices may be used to control the computer of the scanning device 14.

The data processing system at the retail pharmacy location 8 may have more than one scanning device 14. Each of these scanning devices could be similar to any of the scanning devices described above, and each individual scanning device may have a separate computer that operates the individual scanning device. Alternatively, multiple scanning devices may be operated by a central computer that operates each of the individual scanning devices. The individual scanning devices may be connected directly to the tracking system 1, or they may be connected to the tracking system 1 through one or more separate retail pharmacy computers 12. Each of the scanning devices may be simultaneously operated in different operating modes, as described below.

The scanning device 14 may have a number of different operating modes. For example, the scanning device 14 may have a Receiving Mode, a Prescription Fill Mode, a Return to Stock Mode, an E-Pedigree Mode, and a variety of modes for retiring a drug containment unit such as Trash Mode, Salvage Mode and Return to Supplier Mode. In certain implementations, the display 27 of the scanning device 14 may present a menu of the different operating modes and an operator, using one of the input devices, may choose the desired mode.

Figure 4:
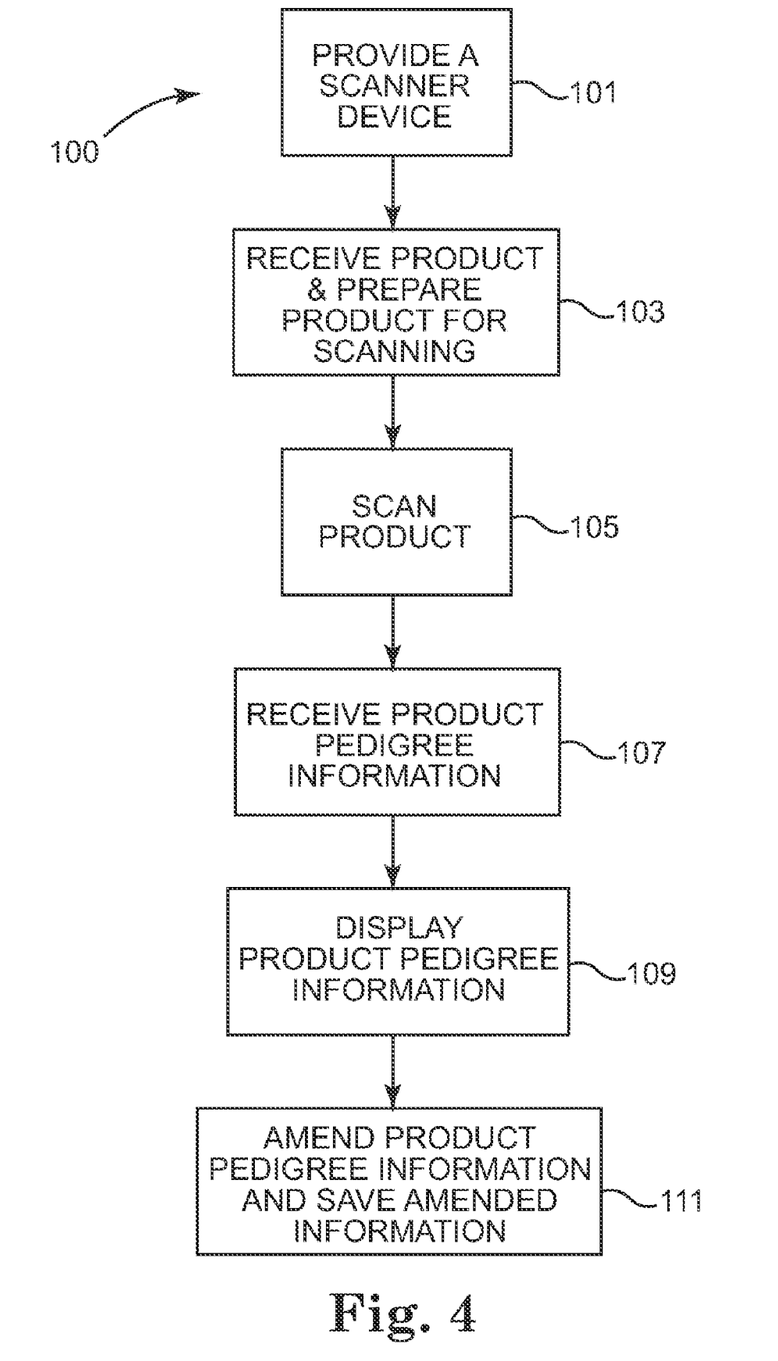
FIG. 4 is a flow chart of an example process for tracking items.

FIG. 4 shows a flow chart of an example process 100 for tracking items. In Receiving Mode, the scanning device is configured to receive a product that has been shipped to the retail pharmacy location 8. In step 101, a scanning device having an RFID reader and a barcode reader is provided. For example, the scanning device may be any of the scanning devices described herein.

As shown in step 103, the retail pharmacy location receives the drugs and prepares the drugs for scanning. In some cases, the drugs are shipped in drug containment units. As discussed above, these drug containment units may be bottles, boxes, or other containers. One or more drug containment units are often shipped in a bulk shipping package. These bulk shipping packages may be shipping packages in which multiple drug containment units may be placed (e.g., a tote). In step 103, the shipment of drugs may be broken down into the smallest packaging unit (i.e., into the individual drug containment units). As an example, a tote may be opened, and one or more bottles, boxes, or other containers may be removed from the tote.

In some cases, there is information that is associated with the bulk shipping package, for example a unique identifier for the tote, a packing list for the tote, and/or an identification of the source of the tote. This tote information may be scanned or otherwise entered into the retail pharmacy data processing system. As further discussed below, the information regarding the tote may be used for requesting information from other elements of the tracking system 1.

In step 105, a drug containment unit may be scanned, for example by a scanning device. As each drug containment unit is scanned, the scanning device may emit an audible or visual indication that the item has been successfully scanned. Or, if the scan was unsuccessful, the scanning device may emit a different audible or visual indication to alert the user.

In some instances, each of the drug containment units may be separately scanned with the scanning device. Because the scanning device has both RFID and barcode readers, the scanning device may scan drug containment units that have either or both of these types of identification systems. As the shipping units are scanned, a unique code for each drug containment unit (e.g., the 2-dimensional barcode or the EPC code) may be read into the scanning device. It is also contemplated that an entire tote may be scanned simultaneously. With simultaneous scanning, drug containment units present in the tote could be individually read by an RFID reader when the entire tote is passed over or near the scanning device. When scanning an entire tote simultaneously, the RFID reader may be configured to alleviate issues with interference between RFID tags, thus facilitating accurate scanning of all of the drug containment units contained in the tote.

Drug containment units may, in certain circumstances, have both a barcode and an RFID tag. In these situations, the identifier associated with the barcode and the RFID tag may be the same identifier or different identifiers. In some implementations, the scanning device may just use the first identifier that is registered by the scanning device and ignore the other identifier. In other implementations, the scanning device may attempt to locate all of the identifiers associated with a particular drug containment unit, and may include all of the identifiers in the pedigree information. As such, the scanning device may use any of the identifiers for identification purposes.

In step 107, the drug pedigree information may be received by the scanning device. As mentioned above, the pedigree information may be received in a number of ways and from a number of different elements of the tracking system 1. In some implementations, information may be pushed to the retail pharmacy location 8 by another element of the tracking system 1. For example, the party that had possession of the drug prior to the drug's arrival at the retail pharmacy could push the information to the retail pharmacy location 8 upon physical delivery to the retail pharmacy location 8. In other implementations, the scanning device 14, or a separate retail pharmacy computer 12, could query another element of the tracking system 1 for the drug pedigree information. In some cases, information scanned from the tote itself may indicate the party or parties who were previously in possession of the drug and the tote number or information from the tote packing list may be used to identify the information that is being requested by the retail pharmacy location 8.

In implementations where each party to the tracking system 1 maintains a portion of the drug pedigree corresponding to the time the party had possession of the drug, the scanning device 14 or a separate computer 12 may send a query to all of the parties to the tracking system 1 that had ever been in possession of the drug. Alternatively, where the latest version of the drug pedigree is maintained by one party (e.g., the last party to have possession of the drug, or a central data processing system), the scanning device 14 or the separate retail pharmacy computer 12 may send a query to that party to obtain the latest version of the drug pedigree. The requested information may then be received by the scanning device 14 or the separate retail pharmacy computer 12.

Although the process diagram of FIG. 4 is shown receiving the drug pedigree information after the drugs are scanned and before the drug pedigree information is displayed, the pedigree information could also be received at other times, such as before the drugs are scanned. For example, where the drug pedigree information is pushed to the retail pharmacy location 8 by another party of the tracking system 1, the drug pedigree information may be received at any time before, during or after step 105 shown in FIG. 4.

In step 109, the drug pedigree information that has been received from the other elements of the tracking system 1 is displayed. In order to display the information, the code that is read from the drug containment unit in step 105 may be compared to the drug pedigree information received from the other elements of the tracking system 1. Using a unique identifier (e.g., the EPC code or a unique identifier for the 2-dimensional barcode) for the drug containment unit, drug pedigree information is associated with the correct drug containment unit within the scanning device 14 and/or within a separate retail pharmacy computer 12.

The drug pedigree information may also be checked for errors, such as for completeness and/or for continuity. To check for completeness, the pedigree information may be checked for the presence of certain types of required information, or for a certain quantity of pedigree information. For example, the pedigree information may only be considered complete if the information contains some or all of a set of tracking information, such as the manufacturer's name, the date of manufacture, the location of manufacture, an NDC, a drug name and description, and an expiration date. To check for continuity in the chain of custody, the dates of all of the physical transfers of the drug may be examined to ensure that there are no suspicious gaps in the chain of custody.

The drug pedigree information may be displayed to a user in a number of ways. For example, as each package of drugs is scanned, the pedigree information for that package may be presented on the display. The information that is presented may be all of the information available with respect to the drug pedigree, or only a portion of the information. In addition to presenting some or all of the drug pedigree information, or in place of presenting the drug pedigree information, the status of the drug pedigree may be presented. For example, if a drug pedigree is available, complete, and has continuity of custody, then an indication of an acceptable drug pedigree status may be presented (e.g., a PASS, or an OK indication). If the pedigree information has been requested from a party to the tracking system 1, but no answer has been received, then an indication that the status is pending may be presented. If there is a gap in the chain of custody, if the pedigree information is incomplete, or if there is any other issue with the pedigree information, or if one or more parties to the tracking system 1 indicate that there is no pedigree information available, then an indication of no complete drug pedigree may be presented (e.g., a FAIL indication). In some implementations, the operator of the scanning device may also access a failed drug pedigree in order to see why it has failed.

As mentioned, the pedigree information may be presented individually for each drug package (i.e., immediately after each individual package unit is scanned). In the alternative, the drug pedigree information may be presented in a composite or summary manner. For example, a list of each of the drugs in a tote may be presented on the display as the individual drug packages are scanned. This list could present all or part of the drug pedigree information and/or the status of the drug pedigree. For example, the list could present the drug name, the barcode identifier and/or the EPC code, and the status of the drug pedigree. In addition to displaying the drug pedigree information and/or pedigree status, the scanning device may also alarm (e.g., an audible or visual alarm) when a drug package has failed and/or the scanning device could highlight the failed drug containment unit on the display.

Additionally, those drug containment units without a valid pedigree may be physically removed from the retail pharmacy's dispensary and placed in a "hold" area. These drug containment units may be kept for a time in order to allow for the pedigree to be supplied, or in order for missing information to be supplied. After a time, a drug containment unit without a passing pedigree may either be returned to the distributor or manufacturer, or may be sent to a salvage operation. In these cases, as further discussed below, the drug containment units may be scanned in Return or Salvage Mode so that the pedigree information will reflect the transfer of the drug containment unit away from the retail pharmacy location.

In step 111, the drug pedigree information may be updated in order to reflect the transfer of the drug to the retail pharmacy location 8. The information about the transfer may include, for example, the date of transfer, the time of the transfer, and the specific parties who performed the transfer. The updated pedigree information may be stored in the scanning device 14, in the separate retail pharmacy computer 12, or in another storage device at the retail pharmacy location 8. Additionally or alternatively, the updated drug pedigree information may be sent to a retailer data center 6 or to a central system 9 for storage. The drug pedigree information may be deleted from the scanning device 14 or the separate retail pharmacy computer 12 after a period of time (e.g., 30 days) in order to provide electronic storage capacity when additional drugs are received.

The steps described above with respect to FIG. 4, although presented in a certain order, could be performed in any suitable order depending on the particular requirements of an application.

Figure 5:
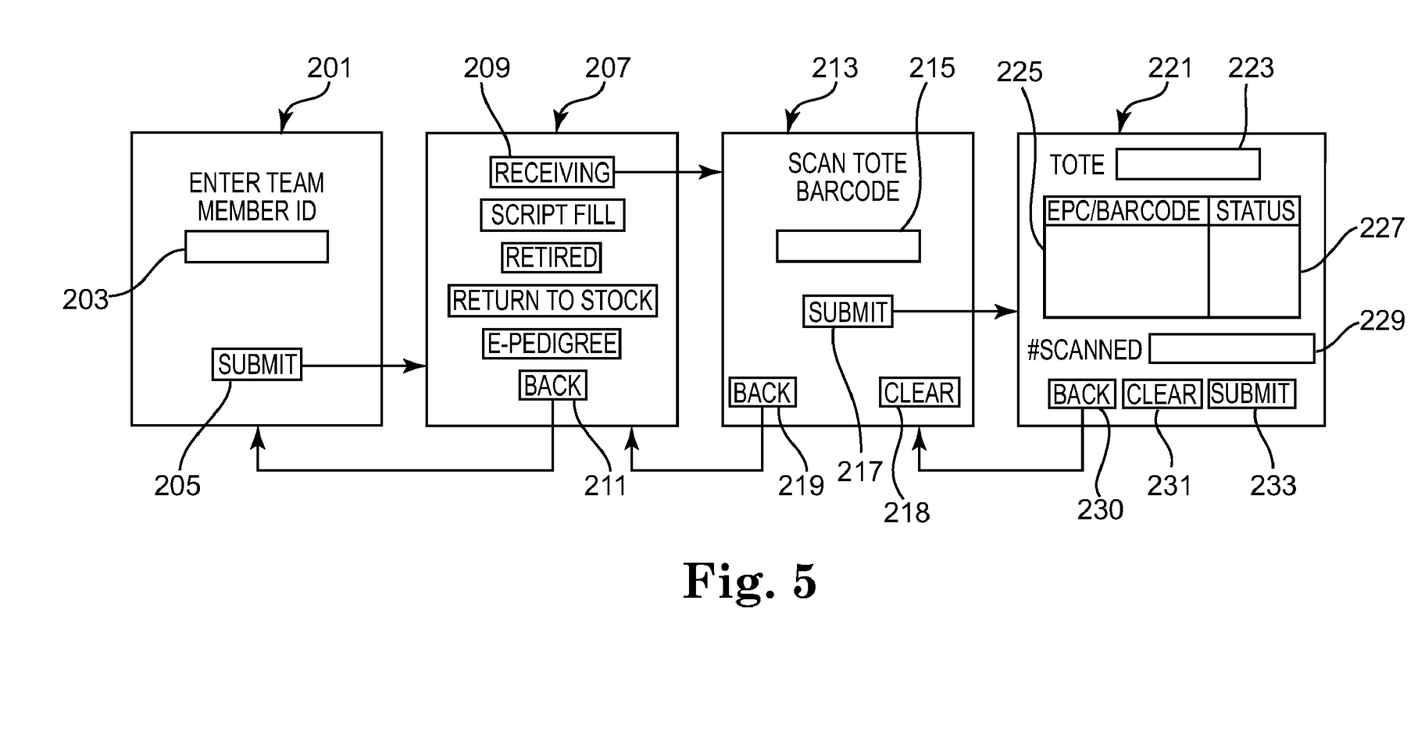
FIGS. 5-9 show sets of example screens for operating a tracking system.

FIG. 5 shows a set of example screens for operating a tracking system to process the receipt of drug containment units at a facility, such as at a retail pharmacy. Screen 201 displays a blank ID field 203 into which a pharmacy team member may enter his or her identification information. Any of the input devices that are described above may be used to enter this identification information. In addition, team members may be issued user-specific identification credentials that include either a barcode or an RFID identifier. The team member may be able to access the system by scanning his or her identification credentials, or may be required to enter both the scanned credential information as well as an ID in the ID field 203. However the team member enters his or her credentials, the team member may then choose the SUBMIT button 205, which confirms the information entered in the ID field 203 of screen 201.

In screen 207, the pharmacy team member may choose between a number of different operating modes (e.g., Receiving, Prescription Fill, Retired, Return to Stock, or E-Pedigree modes), or he or she may choose the BACK button 211, which will return the display to screen 201. When the RECEIVING button 209 is selected, screen 213 may be displayed. As shown, screen 213 has a field 215 to enter a tote identifier, which may be scanned or entered using any of the input devices described above. Screen 213 also has a BACK button 219, which returns the team member to screen 207, a CLEAR button 218, which clears the tote barcode information, and a SUBMIT button 217, which confirms that the information is correct and causes the display to show the next screen 221 in the receiving process.

Screen 221 may include a field 223 for the tote information to be entered and/or displayed and a table with columns 225, 227. In one column 225, the EPC or barcode information for each drug containment unit contained in the tote may displayed, and in the other column 227, the status of each drug containment unit may be displayed. The screen 221 may also have a field 229 for displaying the number of drug containment units that have been scanned. As the team member scans each drug containment unit, the EPC or barcode information and status information may be shown on the screen, along with an incremental count of the number of drug containment units that have been scanned. Screen 221 may also have a BACK button 230, which returns the display to screen 213, a CLEAR button 231, which may clear all of the scanned information from the columns 225, 227, and a SUBMIT button 233, which may submit the information for the scanned drug containment units. The scanning device may also be configured to receive information about the tote itself, such as a packing list for the tote. The scanning device may compare the packing list to the number and types of drug containment units that have been scanned to ensure that all of the drug containment units have been scanned and that the amount and type of drug that has been received matches the packing list.

Figure 6:
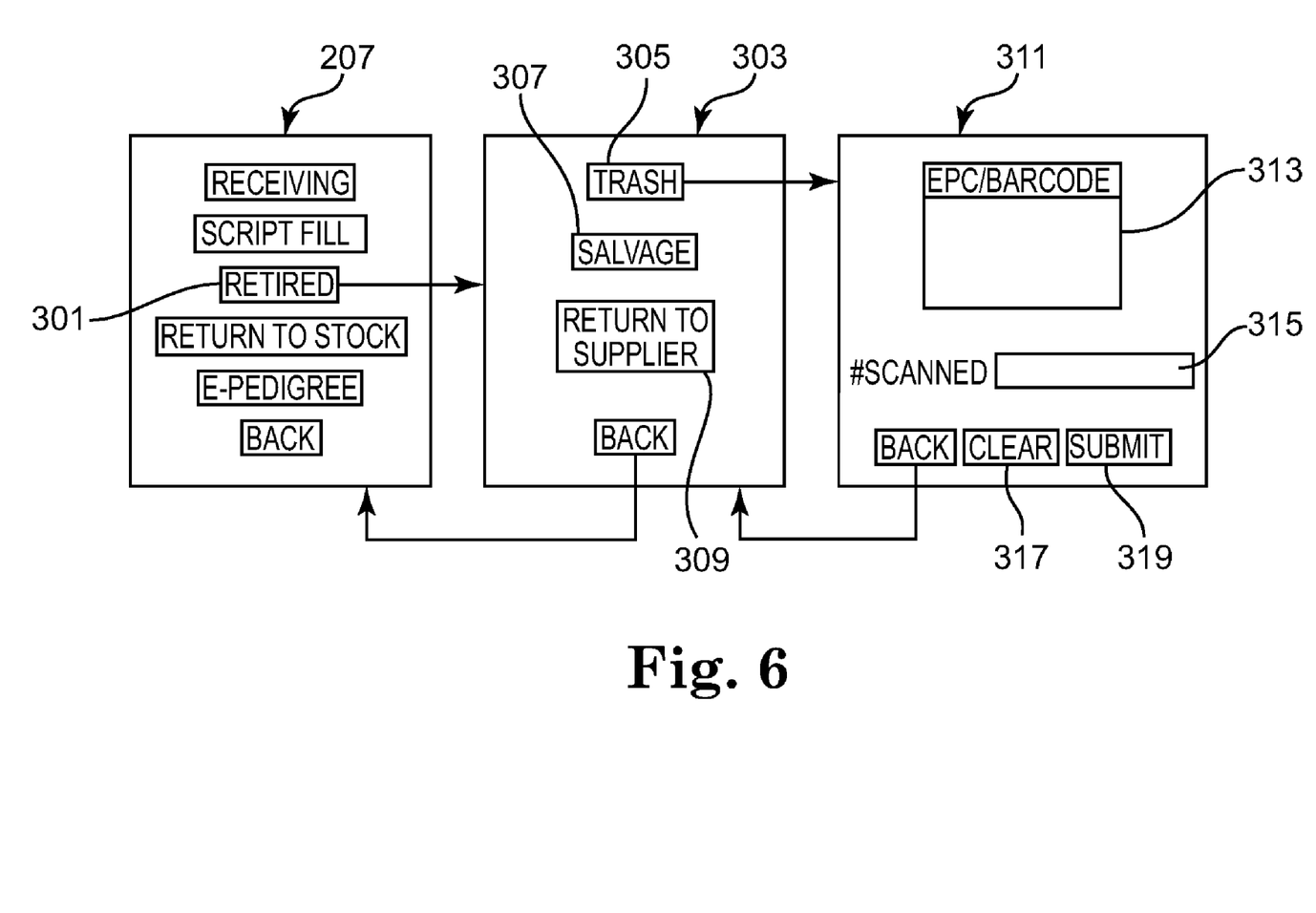

FIG. 6 shows a set of example screens for operating a tracking system to retire one or more drug containment units at a facility. From a mode selection screen 207, the RETIRED button 301 may be chosen, causing screen 303 to be displayed. Screen 303 may have a TRASH button 305, a SALVAGE button 307 and a RETURN TO SUPPLIER button 309, which correspond to each of those respective modes of operation. Depending on the operation that is desired, a team member may choose one of these three buttons 305,307,309. As an example, in FIG. 6, the TRASH button has been chosen, which causes a trash screen 311 to be displayed. The Salvage and Return to Supplier Modes may have screens similar to screen 311. Screen 311 may include a table 313 on which the EPC or barcode identifiers may be listed for each of the drug containment units that are scanned. Screen 311 may also include a field 315 for displaying the number of drug containment units that have been scanned. Screen 311 may also have a BACK button, a CLEAR button 317 that clears any information displayed in screen 311, and a SUBMIT button 319, which confirms that the listed drug containment units are to be trashed.

Each of the different retire modes described above may cause the scanning device to operate in a different manner. For example, in Trash mode, the scanning device may be configured to scan a drug containment unit that is empty, possibly after all of the drug has been dispensed. While in Trash mode, a drug containment unit may be scanned with the scanning device 14, and the scanning device 14 and/or a separate retail pharmacy computer 12 may update the drug pedigree to reflect that the drug containment unit has been trashed or retired at the retail pharmacy location 8. In cases where the drug pedigree is no longer stored at the retail pharmacy location 8 (i.e., when the drug pedigree information is stored at a retail data center 6 and has been deleted from the scanning device 14 and/or the retail pharmacy computer 12), a query for the pedigree information may be sent out by the scanning device 14 and/or the retail pharmacy computer 12 to the appropriate element of the tracking system 1. The information may then be displayed at the scanning device.

In Salvage mode, the scanning device may be configured to scan a drug containment unit that is being sent to a salvage operation. For example, expired drugs may be sent to a third party salvage operation for disposal. While in Salvage mode, the drug containment unit may be scanned with the scanning device 14, and the scanning device 14 and/or the separate retail pharmacy computer 12 may update the drug pedigree to show that the drug package is being salvaged. As in Trash mode, if the drug pedigree information is not stored at the retail pharmacy location 8, an element of the data processing system at the retail pharmacy location 8 may request the information. Further, the updated drug pedigree may be backed up, for example, at a retailer data center 6.

In Return to Supplier mode, the scanning device may be configured to scan a drug containment unit that is being returned (e.g., to the distributor, the manufacturer, or some other party). The drug containment unit may need to be returned, for example, if the drug is expired. While in Return to Supplier mode, the drug package may scanned with the scanning device 14 and the scanning device 14 and/or the separate retail pharmacy computer 12 may update the drug pedigree to show that the drug package is being returned. As discussed above, if the drug pedigree information is not stored at the retail pharmacy location 8, an element of the data processing system at the retail pharmacy location 8 may request the information. Further, the updated drug pedigree may be backed up, for example, at a retailer data center 6.

Figure 7:
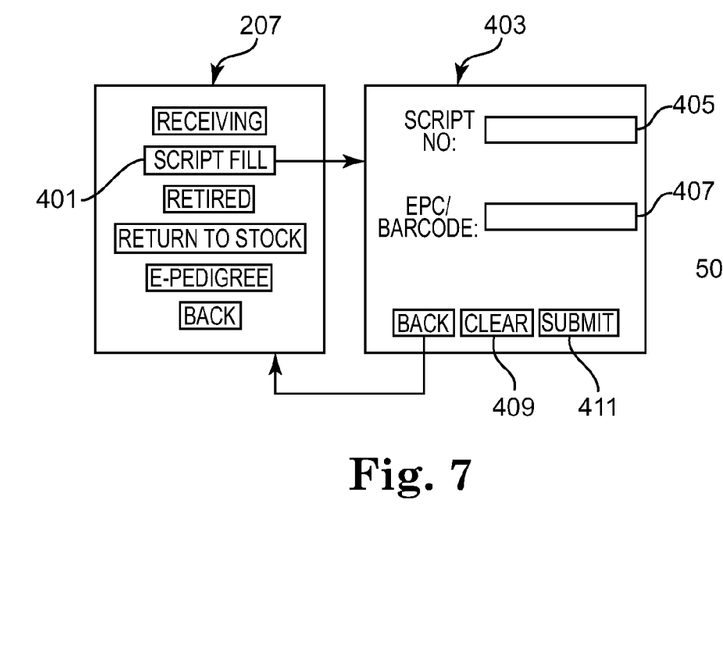

FIG. 7 shows a set of example screens for operating a tracking system to fill a drug prescription. From screen 207, the SCRIPT FILL button 401 may be chosen, which causes screen 403 to be displayed. Screen 403 may include a prescription number field 405, a field 407 for one or more EPC or barcodes, and a BACK button. Screen 403 may also have a CLEAR button 409, which may clear all of the information displayed in the fields 405, 407. In addition, screen 403 may include a SUBMIT button 411, which may confirm that the one or more EPC/barcodes are to be associated with the prescription number. The pharmacy team member may scan a barcode or RFID tag associated with the individual prescription, or may otherwise enter the prescription using an input device. The team member may also scan the one or more drug containment units that will be used to fill the individual prescription. As mentioned above, the scanning device and/or a separate pharmacy computer may decrement the amount of the drug in the one or more drug containment units that is being used to fill the prescription, thus ensuring accurate drug inventory information.

In Prescription Fill mode, the scanning device may be configured to scan a drug containment unit that will be used for filling prescriptions. In addition, a unique identifier may be created for an individual prescription. A barcode label and/or an RFID tag that is encoded with the unique identifier for the individual prescription may also be created. The barcode or RFID tag associated with the individual prescription may be scanned by the scanning device 14. The scanning device 14 and/or a separate retail pharmacy computer 12 may associate the individual prescription (including the prescription amount) with the drug containment unit, and the scanning device 14 and/or the separate retail computer 12 may update the drug pedigree information and/or the prescription information to reflect the filling of the prescription. When drugs still remain in the drug containment unit after the prescription has been filled, the drug containment unit may be returned to the pharmacy inventory. When all of a drug containment unit has been consumed by filling a prescription, then the Trash mode may be used to update the drug pedigree information to reflect this consumption.

The expiration date of a drug containment unit may also be updated. For example, when a drug containment unit is initially opened to fill a prescription, the expiration date of the drug containment unit may be updated to be a certain number of days (e.g., 90 days) from the date that the drug containment unit was initially opened at the pharmacy. Or, the expiration date may remain the same as the original expiration date. In certain implementations, the expiration date may be updated to be the earliest of either the original expiration date, or a certain number of days from the initial opening of the drug containment unit. Any drug containment units that are empty after being used to fill a prescription may be automatically trashed, or a pharmacy team member may separately proceed to Trash mode to trash the drug containment unit.

In addition, because an individual prescription may be associated with one or more particular drug containment units that were used to fill the prescription, the scanning device and/or the separate retail pharmacy computer may be used to determine the drug pedigree of an individual prescription. This may be performed as part of the E-Pedigree mode, or as part of a separate Audit mode, as further described below. In some implementations, as part of the prescription filling process, the scanning device may warn a team member (e.g., by using a visual and/or audible alarm) in certain circumstances. For example, an alarm may be raised to signify that the pharmacy has another drug containment unit that has a more immediate expiration date, that the drug containment unit being used to fill the prescription is expired, that there is another drug containment unit that has already been opened, or that there is a Return to Stock prescription (which will be explained in greater detail below) that may be used. Accordingly, the team member may then choose to retrieve an unexpired drug containment unit that has a more immediate expiration date and/or has already been opened, or a Return to Stock prescription that is available. The scanning device may also verify that the correct drug is being used to fill the prescription and, if not, warn the pharmacy team member as such.

Figure 8:
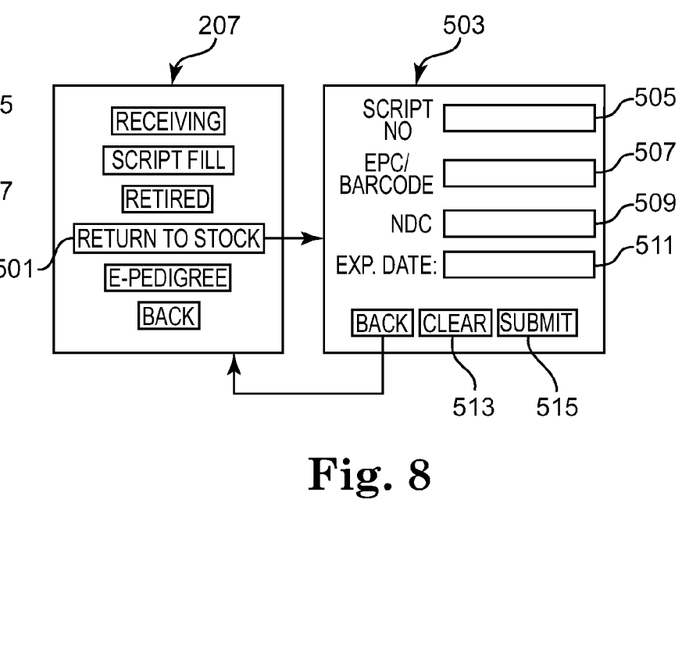

FIG. 8 shows a set of example screens for operating a tracking system in a Return to Stock mode for processing the return of an individual prescription. In this mode, an individual prescription that has not been picked up by a customer within a certain number of days (e.g., 7 days) may be returned to stock. On screen 207, the RETURN TO STOCK button 501 may be chosen, which may cause screen 503 to be displayed. In screen 503, different fields 505, 507, 509, 511 may be provided for the prescription number, the one or more EPC or barcodes that are associated with the prescription number, the NDC, and the expiration date of the drug, respectively. In addition, screen 503 may include a BACK button, a CLEAR button 513, which may clear the information from fields 505, 507, 509, 511, and a SUBMIT button 515, which may confirm that the prescription shown on the screen is to be returned to stock.

Figure 9:
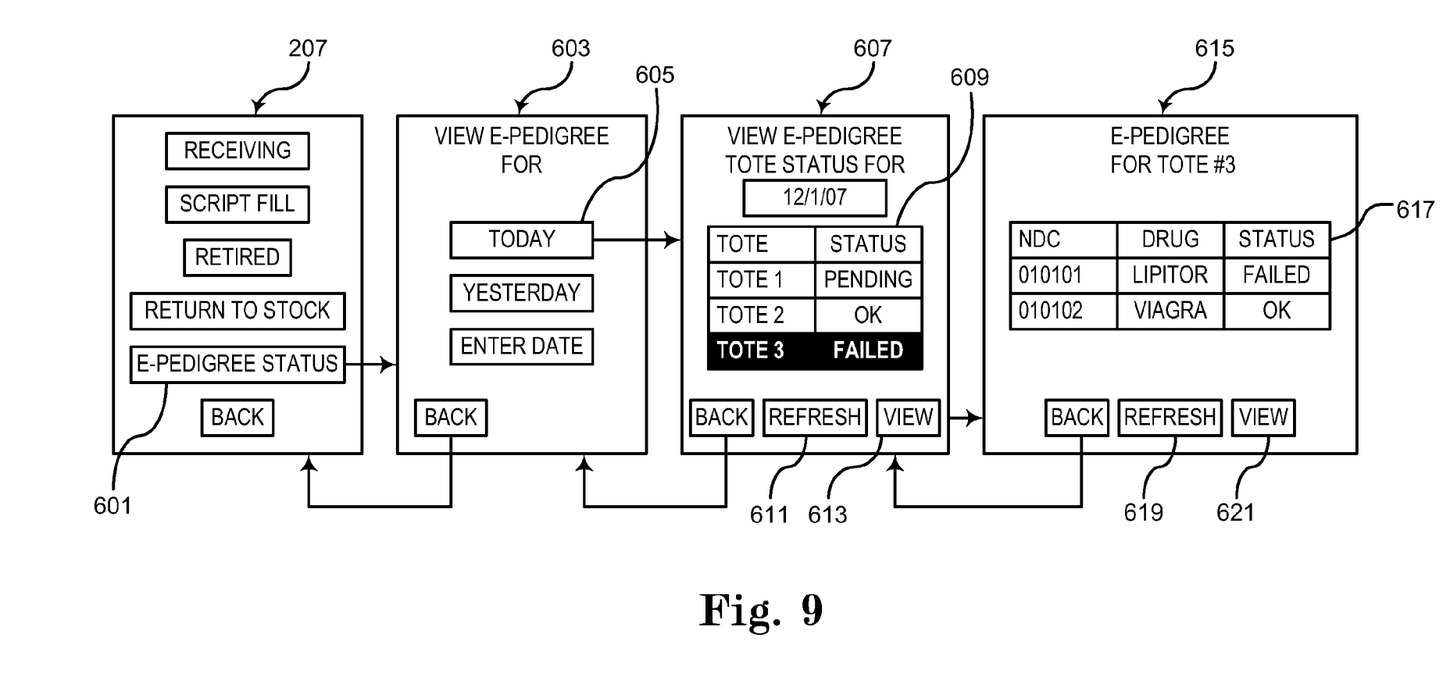

FIG. 9 shows a set of example screens for operating a tracking system to view the E-Pedigree of one or more drug containment units. In E-Pedigree mode, the scanning device is configured to scan a drug containment unit and display some or all of the drug pedigree information and/or a status of the drug pedigree. For example, if a pharmacy team member desired to review the pedigree information and/or the pedigree status of the drugs that were received during a certain time period (e.g., the present day, the previous day, the current month, etc.), the E-pedigree mode may be used for viewing this information. Similar to the Trash mode described above, if the drug pedigree information is not stored at the retail pharmacy location 8, an element of the data processing system at the retail pharmacy location 8 may request the information.

In screen 207, the E-PEDIGREE button 601 may be chosen, and may cause screen 603 to be displayed. Screen 603 may have a number of options for selectable time frames, including TODAY, YESTERDAY, and ENTER DATE. The ENTER DATE button may allow a pharmacy team member to choose a particular date. Screen 603 may also include buttons that allow a team member to enter a date range or to choose a longer period of time, for example the current or the previous month.

As an example, when the TODAY button 605 is chosen, screen 607 may be displayed. Screen 607 may include a field for the date that is being displayed and a table 609 for displaying the tote numbers and the corresponding pedigree status for each tote. The screen 607 may also include a BACK button, a REFRESH button 611, which may refresh the information on the screen, and a VIEW button 613, which may allow a team member to view the detailed information for a tote. For example, in FIG. 9, Tote 3 has been selected, and is shown as shaded on the screen 607. When the VIEW button 613 is chosen with this tote selected, screen 615 is displayed. Screen 615 may list information for the individual tote in a table 617, including the E-Pedigree status for each drug containment unit within a tote. Screen 615 may have a BACK button, a REFRESH button 619 for refreshing the information in screen 615, and a VIEW button 621, which allows a team member to select a drug containment unit and view the detailed information related to the drug containment unit.

Also, as mentioned above, some government agencies require that a drug's pedigree be maintained at a pharmacy and that the drug pedigree be available at all times. The E-Pedigree mode as described herein may be used, for example, by an auditor to ensure that all of the drugs in a pharmacy have an e-pedigree. Alternatively, a separate Audit mode may be provided, in which an auditor may select a drug containment unit from the pharmacy and scan the drug package through the scanning device. The drug pedigree (or lack thereof) and/or the status of the drug pedigree may then be presented on the display, thus providing the auditor with the most up-to-date information about the drug and its handling. As in Trash mode, if the drug pedigree information is not stored at the retail pharmacy location 8, an element of the data processing system at the retail pharmacy location 8 may request the information.

In any of the operating modes described above, the scanning device may provide the operator with an option to print any or all of the following: the contents of the display screen, the pedigree information relating to a particular drug containment unit, the pedigree information relating to a particular bulk shipping package, the pedigree information for a certain type of drug, or the pedigree information for drugs received at the retail pharmacy location 8 during a certain timeframe. In some implementations, the scanning device may also include a report mode in which an operator may also choose from a number of different types of reports. For example, the scanning device may be used to create a report of drug containment units that have expired or that are about to expire, a report on the various items that have been trashed, salvaged, or returned to a supplier over a period of time, or a report related to inventory. Such reports may also be printed by the operator.

A number of implementations have been described. Nevertheless, it will be understood that various modifications may be made without departing from the spirit and scope of the systems and methods described herein. For example, many of the processes are described as being performed in real time, but other implementations may allow the operations to occur using batch processing. Similarly, the steps of various procedures are described as occurring in a certain order, but many of the steps may occur either simultaneously or in a different order than described. Accordingly, other embodiments are within the scope of the following claims.

What is claimed is:

1. A system configured to maintain pedigree information associated with a drug, the system comprising:
   a support structure including an RFID reader and a bar code reader; a master control unit that is operably coupled to the RFID reader and the bar code reader, said master control unit configured to receive product identification data from the RFID reader and the bar code reader;
   a database system communicatively coupled to the master control unit, said database system configured to store pedigree information associated with a plurality of medicament containers, said pedigree information including information relating to a chain of custody of the medicament containers and, for each medicament container, at least two of i) a location and date of manufacture, ii) a batch number, iii) a previous storage location, iv) a quantity of drug in the medicament container, and v) an expiration date;
   a display unit operably coupled to the master control unit and disposed proximate to the support structure, said display unit configured to receive and display said pedigree information to a user; and
   an alarm operably connected to the master control unit that notifies the user if the chain of custody information is incomplete, and displaying a notification if the chain of custody is incomplete wherein, in response to the movement of a medicament container proximate the RFID reader or the bar code reader, the master controller submits a query to the database system, receives said pedigree information, and causes the display unit to display at least a portion of the pedigree information to the user.

2. The system of claim 1, wherein the query includes at least a portion of product identification data associated with the medicament container.

3. The system of claim 1, wherein the display unit includes a touch screen adapted to control the master control unit.

4. The system of claim 1, wherein the barcode reader is disposed in an upper portion of the support structure and the RFID reader is disposed in a lower portion of the support structure.

5. The system of claim 1, wherein the RFID reader is adapted to read RFID tags from a distance of about twelve inches or less.

6. The system of claim 1, further comprising:
   a plurality of data processing systems at a corresponding plurality of drug handling facilities, the data processing systems retrieving and storing the pedigree information;
   a central system communicating with the plurality of data processing systems and the database system, the central system updating the chain of custody information stored in the database system according to input from the data processing systems.

7. A computer-implemented method of tracking drug containment units, the method comprising:
   receiving, at a drug handling facility, a drug containment unit;
   identifying the drug containment unit using a scanning system having an RFID reader, a barcode reader, a computing device configured to electronically communicate with a database system, and a display, wherein identifying the drug containment unit includes moving the drug containment unit proximate the RFID reader or the bar code reader;
   querying the database system to retrieve pedigree information associated with the drug containment unit, wherein said pedigree information includes information relating to a chain of custody of the drug containment unit and at least two of i) a location and date of manufacture, ii) a batch number, iii) a previous storage location, iv) a quantity of drug in the drug containment unit, and v) an expiration date;
   displaying at least a portion of the pedigree information on the display, wherein displaying at least a portion of the pedigree information includes displaying a notification if the chain of custody is incomplete; and
   updating the pedigree information to reflect that the drug containment unit has been received.

8. The method of claim 7, wherein querying the database system includes submitting, from the scanning system, at least a portion of identification information associated with the drug containment unit.

9. The method of claim 7, wherein displaying at least a portion of the pedigree information includes displaying a notification if the pedigree information is unavailable.

10. The method of claim 7, further comprising printing the pedigree information on the drug containment unit.

11. The method of claim 7, further comprising entering into the scanning system handling information associated with a shipping container in which the drug containment unit was packaged.

12. The method of claim 11, wherein the database system is updated to include the handling information.

13. The method of claim 11, wherein the handling information is entered by scanning the shipping container.

* * * * *